United States Patent [19]

Uehara et al.

[11] 4,442,841

[45] Apr. 17, 1984

[54] ELECTRODE FOR LIVING BODIES

[75] Inventors: Masaru Uehara, Komaki; Teruyoshi Uchida, Nagoya; Hirotaka Kojima, Kasugai, all of Japan

[73] Assignee: Mitsubishi Rayon Company Limited, Tokyo, Japan

[21] Appl. No.: 259,112

[22] Filed: Apr. 30, 1981

[51] Int. Cl.³ .............................................. A61B 5/00
[52] U.S. Cl. .................................. 128/635; 204/403; 204/415; 204/431
[58] Field of Search .................... 128/635; 204/195 B, 204/195 P, 403, 415, 431

[56] References Cited

U.S. PATENT DOCUMENTS

| | | | |
|---|---|---|---|
| 4,011,861 | 3/1977 | Enger | 128/419 P |
| 4,041,933 | 8/1977 | Reichenberger | 128/635 |
| 4,073,713 | 2/1978 | Newman | 204/195 P |
| 4,207,146 | 6/1980 | Kunke | 128/635 |

FOREIGN PATENT DOCUMENTS

| | | | |
|---|---|---|---|
| 15075 | 9/1980 | European Pat. Off. | 128/635 |
| 7413253 | 7/1977 | Fed. Rep. of Germany | . |
| 2325930 | 8/1974 | France | . |
| 2215872 | 4/1977 | France | . |
| 55-24968 | 2/1980 | Japan | 204/195 P |
| 2021784 | 12/1979 | United Kingdom | . |

Primary Examiner—Lee S. Cohen
Attorney, Agent, or Firm—Ladas & Parry

[57] ABSTRACT

An electrode for living bodies consisting of a fine metal wire at least part of the surface of which is directly coated with a porous membrane having fine pores of an average pore diameter of greater than 0.01 μm. The electrode makes it possible to measure the oxygen concentration in the blood vessels and in the living tissues with increased stability and improved response characteristics. Particularly good results are obtained when the porous membrane is a non-homogeneous structure using a cellulose acetate.

6 Claims, 9 Drawing Figures

ELECTRODE FOR LIVING BODIES

FIELD OF THE INVENTION

The present invention relates to an improved metal electrode for continuously measuring the change in oxygen partial pressure of living bodies, and more specifically to an improvement in the surface of a metal electrode which makes it possible to take measurement maintaining increased precision and stability in the method of measuring oxygen partial pressure by using a metal electrode which is based upon the principle of polarography.

DESCRIPTION OF THE PRIOR ART

So far, the principle of polarography has been extensively used in the method of measuring the change of the oxygen gas concentration in liquids.

The concentration of oxygen gas in the solution can be measured by using an electrode made of a noble metal such as gold, platinum, silver or the like and an indifferent electrode composed of silver and silver chloride or the like, applying a very small voltage across the two electrodes, reducing oxygen on the surface of a sensitive electrode (cathode), and measuring the current of reduction.

The concentration of oxygen gas (oxygen partial pressure) in the living body seriously affects the living body. In particular, correct and continuous measurement of oxygen partial pressure has been drawing particular attention in regard to newborn babies, anesthesia, cardiosurgery, brain surgery, and surgery of digestive organs. Therefore, the change in the oxygen partial pressure has been measured by inserting the above-mentioned electrode (sensitive electrode) directly into a portion of the living tissue or the blood vessel where it is desired to take measurement. The above measuring method relies upon a diffusion current which results from the gradient of oxygen concentration between the cathode surface and the solution. The living body, however, constantly maintains various motions such as the motion of cardiac muscle and the pulsation of blood. Therefore, the diffusion current is greatly affected, and makes it difficult to measure precisely small oxygen partial pressures.

Extensive study has been conducted in order to improve the above-mentioned defects. For example, there have been proposed a composite electrode (U.S. Pat. No. 3,957,613) which has sensitive electrode, indifferent electrode and electrolyte that are accommodated in an oxygen-permeable membrane, or a method in which the surface of a sensitive electrode is covered with a hydrophilic water-swelling membrane such as polyhydroxyethyl methacrylate, cellophane, or the like, so that oxygen is permitted to move onto the surface of the electrode via water which is captured among the polymer molecules (U.S. Pat. No. 3,912,614). Some of these electrodes and methods have been put into practice.

The above-mentioned type of electrode is of large size and can be inserted only into particular sites such as large blood vessels, while the above-mentioned method has a measuring sensitivity which changes depending upon the state in which the water-swelling membrane is held, has poor sensitivity, and the membrane is easily broken when it is dried.

There has further been proposed a method in which a dense film-like membrane of cellulose acetate is formed on the surface of the electrode by adhering a solution of cellulose acetate on the surface of the electrode followed by the evaporation of the solvent. In practice, however, the diffusion rate of oxygen gas in the membrane is small, i.e. it is difficult to control the sensitivity, and the response speed is poor.

SUMMARY OF THE INVENTION

There is therefore a need for an electrode for living bodies, which can be inserted into any site in the living tissue or in the blood vessel, and which is capable of continuously measuring the oxygen partial pressure maintaining good stability, precision and sensitivity without being affected by the motion of the tissue or the blood.

According to the invention there is provided an electrode for living bodies, wherein at least a portion of the surface of a fine wire electrode composed of an electrically conductive metal is directly coated with a high molecular porous membrane having fine pores of an average pore diameter of greater than 0.01 $\mu$m.

Figure 1:
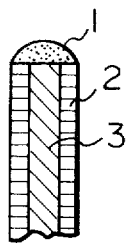
FIGS. 1, 3 through up to 9 are cross-sectional views of electrodes for living bodies according to the present invention.

In these drawings, reference numeral 1 denotes a porous membrane, 2 denotes an electrode protection member having electrically insulating property, 3 denotes a fine wire-like metal electrode, 4 denotes a thorn, 5 denotes a non-slip, 6 denotes an electrode protection member, 7 denotes a dense layer on the surface of the membrane, 8 denotes a porous layer in the membrane, 9 denotes fine pores, and 10 denotes a polymer layer.

DESCRIPTION OF THE PREFERRED EMBODIMENTS

The electrode for living bodies according to the present invention consists of a fine wire-like metal electrode at least part of the surface of which is covered with a porous membrane of a particular construction.

According to the principle of polarography, the solution on the surface of the electrode must be maintained stable when it is attempted to measure the diffusion current relying upon the gradient of oxygen concentration between the solution and the interface of the cathode.

The inventors of the present invention have found the fact that a stable contacting state can be established between the surface of the cathode and the solution if the surface of the cathode is covered with a porous membrane of a particular structure. By inserting the electrode directly into the living body, it is possible to measure the change in the oxygen partial pressure while maintaining good precision and response characteristics without being affected by the motion of the tissues or the blood.

The porous membrane of a particular structure referred to in the present invention has fine pores of an average pore diameter of greater than 0.01 $\mu$m. Fine pores in the porous membrane must have open structure. Therefore, when the electrode is inserted in the blood or in the tissue, the membrane quickly absorbs the liquid to form a stable layer of liquid membrane on the surface of the electrode. The oxygen gas in the external liquid quickly diffuses into the liquid in the membrane and reaches the surface of the electrode. When the average pore diameter is smaller than 0.01 μm, formation of the layer of liquid membrane is delayed when the dry electrode is inserted in the blood vessel or the tissue, and extended periods of time are required before stable response is obtained. The porous membrane may have a homogeneous structure (homogeneous pore diameter over the whole membrane) or a nonhomogeneous structure as will be mentioned later, provided the average pore diameter is greater than 0.01 μm.

The upper limit of the pore diameter is determined by taking into consideration the structure of the porous membrane, strength, and the site where the measurement is to be taken. With the electrode for living bodies of the present invention, the surface of the membrane comes into frequent contact with the blood. Therefore, if the pores in the surface of the membrane have large diameters, hematocytes such as red blood cells in the blood could pass through the pores or clog the pores, so that the oxygen gas penetrates therethrough less easily. From this point of view, the pore diameter of the membrane should be smaller than 0.7 μm, and preferably smaller than 0.5 μm. From the viewpoint of the rate of forming the stable layer of the liquid membrane and the permeation of the oxygen gas, the pore diameter should be large.

Figure 2:
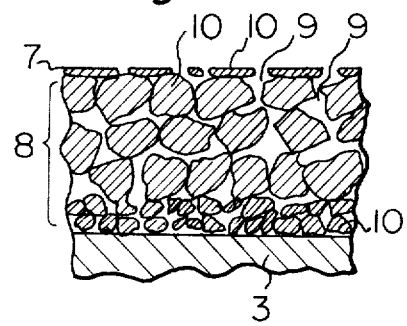
FIG. 2 is a schematic diagram illustrating, in cross-section, the porous membrane which covers the surface of the electrode.

To deal with the above-mentioned conflicting requirements, a preferred embodiment employs a porous membrane of a non-homogeneous structure. Thus, a thin and dense layer having an average diameter of 0.01 to 0.7 μm, preferably an average diameter of 0.01 to 0.5 μm, is formed on the surface (outer surface) of the membrane, in such a manner that the average pore diameter of the inner layer of the membrane is greater than the pore diameter of the dense layer on the outer side. The electrode covered with such a membrane exhibits particularly stable and rapid response characteristics. This embodiment does not restrict the structure in the membrane (inner layer), but employs the membrane of any structure provided the pore diameter of the inner layer is greater than the pore diameter of the dense surface layer of the outer side. Namely, even when the pore diameter of the inner layer is selected to be greater than the diameters of the hematocytes and thrombocytes, such particles are prevented from passing through the surface layer, i.e. such particles do not enter into the membrane, and liquid components only are allowed to quickly infiltrate thereinto. When the porous membrane is produced by a wet-type membrane-making process, cavities (macrovoids) are formed in the inner layer of the membrane having effective diameters ranging from ten and several microns to several tens of microns. The macrovoids are open to fine pores having an average diameter of submicrons to several microns in the vicinities thereof, and do not interrupt the infiltration of the liquid. Therefore, the porous membrane according to the present invention may contain macrovoids. The interior of the membrane may also be of a multi-layer construction. As schematically illustrated in FIG. 2, the pores of the inner layer have diameters that become smaller toward the surface of the electrode. Therefore, the oxygen gas can quickly diffuse into the membrane to reach uniformly the surface of the electrode. The upper limit of the average pore diameter of fine pores in the membrane should preferably be smaller than 5 μm from the viewpoint of the strength of the membrane and uniform diffusion of the oxygen gas toward the electrode.

The average diameter referred to in the present invention is found by observing the cross section of the porous membrane through an electron microscope and by averaging the measured effective diameters of fine pores. The macrovoids, however, are not regarded as fine pores and are not included in the calculation for finding the average diameter of pores.

The greater the porosity of the porous membrane, the higher the sensitivity of the electrode. The porosity, however, is determined relative to the physical strength of the membrane. A preferred range lies from 20 to 60%.

The thickness of the porous membrane which covers the electrode of the present invention is determined by the physical strength of the region where the electrode is to be used and the stability from the standpoint of producing the electrodes. Roughly, however, the thickness of the porous membrane ranges from 10 to 200 microns, and preferably from 30 to 100 microns.

If the thickness of the membrane exceeds 200 microns, the response speed is greatly decreased. On the other hand, when the thickness of the membrane is smaller than 10 microns, a stable layer of liquid having a gradient of oxygen concentration on the surface of the electrode is extremely easily disturbed, and it becomes difficult to achieve the object which is contemplated by the present invention. Further, the thickness of the dense layer on the surface should be as small as possible but within a range in which it provides the requirement of physical stability, such that the oxygen gas can be quickly diffused. Thus contamination to the membrane and pulsating motion from the external source should be prevented by the outermost dense layer having a thickness as small as possible, and the layer of liquid having a gradient of oxygen concentration should be stably formed by the inner layer having pores of large diameters.

The porous membrane or non-homogeneous membrane having such a particular structure can be formed by a method in which a dense film formed on the surface of the electrode is swollen with a swelling agent, and is substituted by a non-solvent to form pores, by a method in which a polymer solution is adhered onto the surface of the electrode, and is coagulated by removing the solvent therefrom in a non-solvent which is compatible with the solvent, or by any other methods. The pore diameter can be adjusted by the combination of solvent and swelling agent, concentration of the membrane-forming material, composition of the coagulating bath, and temperature of the coagulating bath. The non-homogeneous membrane having porous structure referred to in the present invention can be formed preferably by the latter method, i.e. by the wet-type membrane-making method.

According to the wet-type membrane-making process, the non-homogeneous membrane having a dense surface layer or the non-homogeneous membrane having gradient in the pore diameter and in the porosity, can be relatively easily formed by maintaining appropriate timing from the step of adhering a solution of membrane-forming material to the step of removing the solvent in the coagulating bath, by controlling the temperature in the coagulating bath, and by repeating the adhesion and the coagulation operation.

As required, the thus obtained porous membrane will be further subjected to the annealing to adjust the pore diameter or to adjust the strength of the membrane.

According to the present invention as mentioned above, the porous membrane is directly formed on the surface of a fine wire-like electrode, which differs from the conventional method according to which the porous membrane or membrane for selective permeation is separately prepared, and is mounted on the surface of the electrode by using an O-ring or the like. According to the present invention therefore, the porous membrane is firmly adhered on the electrode and does not peel off when it is being used.

The porous membrane of the present invention can be obtained from a hydrophilic polymer such as cellulose, cellulose nitrate, collodion, cellulose acetate, a copolymer of a hydrophilic monomer, e.g., vinylpyrrolydone, or hydroxyethyl methacrylate, or from a hydrophobic polymer such as polyethylene, polypropylene, polystyrene, polyester, Teflon, silicone, or nylon. These polymers should be easily dissolved and swollen by a solvent or swelling agent. Among them, the cellulose acetate is particularly preferred from such a standpoint that the pore diameter of the membrane can be easily controlled, the strength of the membrane can be increased, antithrombic property is exhibited, the membrane can be easily produced by the wet-type process, and the like, which are required for the electrode for living bodies of the present invention. It was found that the membrane of cellulose acetate can be easily and firmly formed on the surface of the electrode, and the pore diameter can be controlled in the porous membrane depending upon such conditions as the solution concentration, temperature of the coagulation bath and the timing of coagulation, if the cellulose triacetate having an acetyl content of greater than 42% is dissolved in the formic acid to mature it while hydrolyzing the acetyl groups with the formic acid, and if the formic acid solution of acetyl cellulose having an acetyl content which is adjusted to 10 to 40% is adhered onto the surface of the electrode, followed by the wet-type coagulation using water as a non-solvent.

The electrode for living bodies according to the present invention is directly inserted into the living body or inserted into the living body using any auxiliary means. This, however, in no way restricts the present invention.

However, since the electrode will be directly inserted into the tissue, the metal electrodes should have a diameter of smaller than 300 microns and should also have flexibility.

A hard wire having a diameter of greater than 300 microns may often be removed by the motion of the tissue while the measurement is being taken, and hence requires an auxiliary fitting to fix it.

Figure 3:
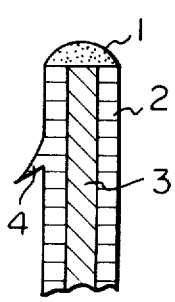
Figure 4:
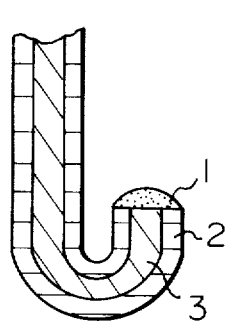
Figure 5:
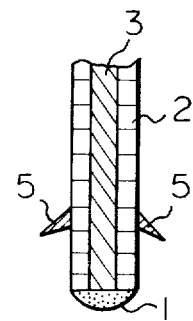
Figure 7:
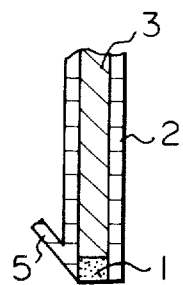
Figure 9:
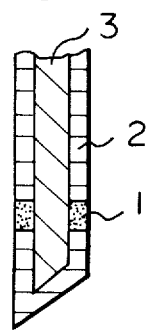

Below are described the shapes of the electrode. As shown in FIGS. 1 and 3 through up to 8, the electrode for living bodies according to the present invention consists of a fine metal wire 3 which is protected by a protection member 2 made of an insulating material, the tip of the fine metal wire 3 being covered with a membrane 1. The area of application of the membrane, however, is in no way restricted. Namely, the porous membrane may be applied to the side portions of the fine wire in the form of a ring as shown in FIG. 9. Further, in order that the electrode can not be removed from the tissue of the living body by the motion of the living body, a barb 4 may be formed as shown in FIG. 3, or a non-slip means 5 may be formed as shown in FIGS. 5 and 7. In place of forming non-slip means 4 or 5, a wire may be wound around the electrode in the form of a spiral. The non-slip means may be made of the same material as the insulator or may be made of a different material. FIG. 4 shows the electrode the tip of which is curved to prevent removal.

Figure 6:
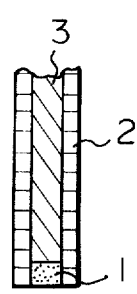
Figure 8:
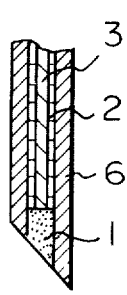

The porous membrane according to the present invention exhibits physical stability which is strikingly improved over the conventional water-swelling membranes such as of polyhydroxyethyl methacrylate which swells with water. The porous membrane according to the present invention will be broken when it is repeatedly used. To cope with this inconvenience, the electrode can be constructed in the shapes as shown in FIGS. 6 to 8. Namely, a recessed portion 1 is formed at the tip of the electrode which consists of an electrode portion 3 and an electrode protection portion 2, and the exposed portion of the metal electrode in the recessed portion is filled with the porous membrane 1 of the present invention. Referring to FIG. 8, the insulating protection member is further coated with a protection member 6, a recessed portion is formed in space defined by the protection member 6 and the electrode, and is filled with the porous membrane 1. In this case, the protection member 6 may or may not have electrically insulating property. In other words, the protection member 6 can be made of any material.

With the electrode having the shape of FIG. 8, the porous membrane is particularly protected for stability.

The fine metal wire may be made of any material provided it has electric conductivity. From the viewpoint of preventing corrosion and maintaining safety in the living body, however, the fine metal wire should be made of platinum.

The electrode for living bodies, having porous membrane on the surface thereof exhibits further increased response characteristics if it is kept immersed in physiological saline water, ion-exchanged water or dialysed water.

The invention will be explained below in further detail in conjunction with working examples.

EXAMPLE 1

Cellulose triacetate having an acetyl content of greater than 42% was uniformly dissolved in 98% aqueous formic acid in an amount of 5% in solid content, and was matured at ordinary temperature to obtain a formic acid solution of cellulose acetate having an acetyl content of 22%.

The tip of a platinum wire having a diameter of 100 microns coated with an electrically insulating polymer was cut by a sharp knife at right angles with the lengthwise direction thereof, so that a new platinum surface was exposed.

The tip of the platinum wire was brought into contact with the solution of cellulose acetate having the acetyl content of 22%, so that the solution was adhered onto the tip. The tip was then quickly immersed in the ion-exchanged water (room temperature) to remove the solvent, and there was formed a gelated membrane.

The above-mentioned operation was repeated three times to form a layer of a thickness of about 40 microns uniformly on the surface of the tip.

The layer was washed well with the ion-exchanged water, dried at normal temperature, put into a drier heated at 180° C., and was annealed for 10 minutes.

The thus adhered layer was solidified. It exhibited white color, tough property and was firmly attached to the surface at the tip of the platinum wire.

Observation through an optical microscope revealed the formation of a layer of a thickness of about 30 microns on the surface of the tip. Further, the cross section of the layer was photographed by using scanning type electron micrograph, and it was confirmed that the layer was composed of a porous membrane having an average pore diameter of about 200 angstroms. Although the pore diameter was measured relying upon the magnification of the photograph, variance in the distribution of pore diameter was very small or, in other words, the pore diameter was highly uniform.

The polymer coating at the other end of the platinum wire was peeled off, and was connected as a sensitive electrode to a detection head of a polarographic oxygen gas partial pressure measuring instrument POG-200 which was manufactured by Unique Medical Co.

Further, an electrode of the type of silver/silver chloride was connected as an indifferent electrode, and the tips of the two electrodes were inserted in a closed circuit in which the physiological saline water circulated maintaining a temperature of 37° C. and at a flow rate of 500 ml per minute.

Then, the air was introduced into the closed circuit (having a vent hole) until the oxygen gas was saturated under normal pressure. Then, a voltage of −0.6 volt was applied across the two electrodes to initiate the measurement.

When a platinum wire of which the tip was uncovered with membrane was used for the purpose of comparison, the output varied so greatly that it was not possible to take the measurement.

The platinum wire of which the tip was coated with the layer, on the other hand, exhibited a constant value (current) which could be converted into an oxygen partial pressure of 150 mmHg.

Next, in order to detect the response speed, two kinds of physiological saline waters having different oxygen concentrations (Oxygen partial pressure of 150 mmHg by the air, and oxygen partial pressure of 75 mmHg by the mixture gas of nitrogen and oxygen) were alternatingly sent into the electrode vessel using a three-way cock, to measure the time until the equilibrium was reached after the conversion or to measure the time until 90% of the change was exhibited (abbreviated as $T_{90}$).

As equlibrium current was confirmed for 10 minutes using the physiological saline water having the oxygen partial pressure of 150 mmHg. The cock was then switched to introduce another physiological saline water having the oxygen partial pressure of 75 mmHg. Excellent response characteristics were confirmed after the time $T_{90}$ of 30 seconds.

Thus, by using the platinum wire coated with the porous membrane, the oxygen partial pressure in the fluid could be accurately and stably measured.

EXAMPLE 2

The tip of a platinum wire of a diameter of 100 microns coated with polyurethane was cut by a sharp knife at right angles with the lengthwise direction thereof to expose the new surface of platinum wire. The tip of the platinum wire was brought into contact with the formic acid solution of cellulose acetate (acetyl content, 22%) of Example 1 so that the solution was adhered onto the tip. The tip was then quickly immersed in the ion-exchanged water of 50° C. to remove the solvent, and there was formed a gelated film. Then, the platinum wire on which was formed the gelated film was brought into contact again with the above solution of cellulose acetate, to adhere the solution onto the gelated film. The solution was slightly dried in the air at ordinary temperature, and was immersed in the ion-exchanged water maintained at 50° C. A porous membrane was formed on the tip of the platinum wire. The porous membrane was washed well with the ion-exchanged water, dried in the air at room temperature, and was put into a hot-air dryer heated at 180° C. to thermally treat it for 10 minutes. Observation of the platinum wire through a microscope revealed the film having a thickness of about 20 microns. Further, the cross section and surface of the membrane covering the platinum wire were photographed by a scanning-type electron micrograph. The membrane possessed a double-layer construction in cross section, the thickness of the outer layer was about 2 microns, and the thickness of the inner layer was about 18 microns. The outer layer uniformly contained pores having an average pore diameter of about 0.3 microns, and the inner layer consisted of a uniform porous membrane having an average pore diameter of 3.5 microns. By using the thus obtained platinum wire electrode, the oxygen concentration in the physiological saline water was measured using the same measuring instrument as that of Example 1. According to this example, the physiological saline water was circulated at a rate of 100 ml per minute, the saline water was saturated with the air, and the measurement was initiated. The measurement of current indicated a constant value without affected by the flow of the liquid. The electric current by the saturated air was converted into 150 mmHg, and the nitrogen gas was introduced into a gas exchange portion in the circulating system instead of introducing the air. At this moment, the electric current linearly decreased from a value that corresponds to 150 mmHg to a stable value that corresponds nearly to 0 mmHg. With this value as being 0 mmHg, a calibration curve was found. Then, the physiological saline water was saturated with the mixture gas consisting of oxygen gas and nitrogen gas at a suitable ratio, to find the values. The results were nearly in agreement with the calibration curve that was found earlier. For the purpose of comparison, measurement was taken under the same conditions by using a platinum electrode without coated with the porous membrane. In this case, the electric current varied so greatly by the flow of liquid that it was difficult to measure the value. Further the electrode exhibited greatly improved response characteristics and stability as compared with the electrode having a homogeneous porous membrane at the tip.

EXAMPLE 3

The coated platinum wires prepared in Examples 1 and 2 were inserted into the cardiac muscle of a dog and into the artery of the heart by using a catheter to measure the changes in the heart that are caused by the blood vessels which govern the cardiac muscle, by the stricture and opening of the artery of the heart or by the injection of a cardiotonic drug, as well as to measure the change in oxygen partial pressure in the cardiac muscle caused by the pace maker.

The membrane was not damaged when it was inserted into the site or removed from the site. Immediately after washed, the electrode could be sufficiently used again without losing performance.

The increase or decrease of oxygen concentration due to the stricture and opening of the blood vessel as controlled by the doctor, and the increase or decrease of oxygen concentration corresponding to the change in the motion of cardiac muscle, could be detected maintaining a response of shorter than 10 seconds. Namely, it was recognized that the electrode of the present invention possessed highly accurate and quick response characteristics.

EXAMPLE 4

A polyurethane-coated platinum wire having a diameter of 100 microns was cut by a sharp knife at right angles with the lengthwise direction thereof, so that new platinum surface was exposed. The thus exposed surface at the tip was brought into contact with the formic acid solution of cellulose acetate (acetyl content, 22%) prepared in Example 1, such that the solution was adhered onto the tip. The tip was then immediately immersed in the ion-exchanged water maintained at 50° C. to remove the solvent and to form a gelated film. The above operation was repeated twice to form uniformly a membrane on the surface at the tip of the platinum wire. The membrane on the platinum wire was brought again into contact with the above solution of cellulose acetate, slightly dried in the air at room temperature, immersed in the ion-exchanged water maintained at 55° C., to remove the solvent and to form a porous membrane on the tip of the platinum wire. The porous membrane was then sufficiently washed with the ion-exchanged water, dried in the air at room temperature, and was heat-treated in a hot-air drier heated at 180° C. for 10 minutes. Observation of the cross section and surface of the membrane of the platinum wire through a scanning-type electron microscope revealed the fact that the film possessed three-layer structure, the outer layer having a thickness of about 2 microns and an average pore diameter of about 0.3 micron, the second layer having a thickness of about 15 microns and an average pore diameter of about 5.1 microns, and the third layer having a thickness of about 7 microns and an average pore diameter of 1.7 microns. By using the platinum wire coated with the porous membrane having the multi-layer structure as mentioned above, the oxygen partial pressure was measured using the circulating system and apparatus of Example 1. It was found that there exists a linear relation between the oxygen partial pressure in the circulating system and the measured current value. The electrode was inserted into the jugular vein and the S-shaped intestinal tract of the colon of a dog, to measure the oxygen partial pressure. Accurate and stable current values were obtained that could not be obtained with a bare platinum wire electrode.

Further, the electrode exhibited greatly improved response characteristics and stability as compared with the electrode having a homogeneous porous membrane at the tip.

COMPARATIVE EXAMPLE 1

Cellulose acetate having an acetyl content of about 40% was dissolved in acetone in an amount of 10% in solid content. To this solution was brought into contact a new platinum surface of a platinum wire having a diameter of 100 microns that was prepared in the same manner as in Example 1, so that the solution was adhered thereto. The solution was then dried in the air at room temperature.

The above operation was repeated twice to adhere the film of cellulose acetate onto the surface of the platinum electrode. The electrode was put into a drier heated at 180° C. to effect the annealing for 10 minutes. The thickness of the thus obtained film was 20 microns. Observation of the cross section of the film through a scanning-type electron microscope did not reveal the formation of homogeneous membrane having pores of pore diameters of greater than 0.01 μm.

Using this electrode, the physiological saline water having an oxygen gas partial pressure of 150 mmHg by blowing the air in the same manner as in Example 1, was electrolyzed at a temperature of 37° C. to measure current values of electrolysis.

The initial response was almost zero, and a constant response of a small sensitivity was obtained after more than three hours have passed. In the same system, furthermore, a response time ($T_{90}$) from the oxygen partial pressure of 150 mmHg to 75 mmHg was found. The response time $T_{90}$ was longer than 10 minutes.

We claim:

1. A fine wire electrode for measuring gas concentration in living bodies comprising an electrically conductive metal, a high molecular porous membrane of a thickness ranging from 10 to 200 μm directly coated on at least a portion of a surface of said electrically conductive metal, said membrane comprising a surface layer having fine pores of an average pore diameter greater 0.01 μm and smaller than 0.7 μm and an inner layer which is contiguous with the surface layer having pores of an average diameter greater than that of the surface layer, and an insulating material sheathing the remaining surface of said conductive metal.

2. An electrode for living bodies according to claim 1, wherein the porous membrane consists of cellulose acetate.

3. An electrode for living bodies according to claim 2, wherein the cellulose acetate has an acetyl content of 10 to 40% and is obtained by maturing and hydrolyzing a formic acid solution of cellulose triacetate having an acetyl content of greater than 42%.

4. An electrode according to claim 1, wherein a recess is formed a terminal tip of the electrode between the metal and the insulation material, the porous membrane being located within the recess.

5. An electrode according to claim 1, wherein a nonterminal portion of the surface of the metal is directly coated with the porous membrane the remaining surface being sheathed with said insulating material.

6. An electrode according to claim 1, wherein the electrically conductive metal comprises a wire having a diameter of less than 300 μm.

* * * * *